(12) United States Patent
Yabutani et al.

(10) Patent No.: US 9,581,609 B2
(45) Date of Patent: Feb. 28, 2017

(54) AUTOMATIC COAGULATION ANALYZING APPARATUS AND ANALYZING METHOD

(71) Applicant: HITACHI HIGH-TECHNOLOGIES CORPORATION, Tokyo (JP)

(72) Inventors: Chie Yabutani, Tokyo (JP); Akihisa Makino, Tokyo (JP); Sakuichiro Adachi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/777,550

(22) PCT Filed: Mar. 19, 2014

(86) PCT No.: PCT/JP2014/057601
§ 371 (c)(1),
(2) Date: Sep. 16, 2015

(87) PCT Pub. No.: WO2014/162878
PCT Pub. Date: Oct. 9, 2014

(65) Prior Publication Data
US 2016/0291046 A1    Oct. 6, 2016

(51) Int. Cl.
G01N 33/86    (2006.01)
G01N 21/51    (2006.01)
G01N 35/00    (2006.01)

(52) U.S. Cl.
CPC ....... *G01N 35/00693* (2013.01); *G01N 33/86* (2013.01); *G01N 2035/0097* (2013.01); *G01N 2035/00702* (2013.01)

(58) Field of Classification Search
CPC ................................ G01N 33/86; G01N 21/51
(Continued)

(56) References Cited

U.S. PATENT DOCUMENTS 3,458,287 A * 7/1969 Gross ................... G01N 21/272
356/39
4,252,536 A * 2/1981 Kishimoto ......... G01N 33/4905
356/36
(Continued)

FOREIGN PATENT DOCUMENTS

EP    0 932 041 A2    7/1999
JP    10-123140    *    5/1998
(Continued)

OTHER PUBLICATIONS

International Preliminary Report on Patentability received in corresponding International Application No. PCT/JP2014/057601.
(Continued)

*Primary Examiner* — Arlen Soderquist
(74) *Attorney, Agent, or Firm* — Mattingly & Malur, PC (57) ABSTRACT

A detection unit 113 measures scattered light intensity E as a coagulation index. A first curve fitting function 120B-a c calculates, at a predetermined time interval, a parameter for an approximate curve of a coagulation curve by curve fitting, based on the measured scattered light intensity E. An early reaction checking function 120B-b determines whether there is a lag phase as an early coagulation index change, based on the parameter for the approximate curve. The parameter has been calculated at the predetermined time interval by the first curve fitting function 120B-a. A clotting time calculation function 120B-f calculates clotting time, based on whether there is the lag phase.

6 Claims, 8 Drawing Sheets

(58) Field of Classification Search
USPC .................. 422/73; 436/69, 164; 702/19, 32
See application file for complete search history.

(56) References Cited

U.S. PATENT DOCUMENTS

| | | | | | |
|---|---|---|---|---|---|
| 4,720,787 | A | * | 1/1988 | Lipscomb | G01N 21/82 422/73 |
| 4,766,083 | A | * | 8/1988 | Miyashita | G01N 21/47 356/340 |
| 5,114,860 | A | * | 5/1992 | Hayashi | G01N 33/86 356/338 |
| 6,432,657 | B1 | * | 8/2002 | Kikuchi | G01N 33/86 435/13 |
| 6,524,861 | B1 | * | 2/2003 | Anderson | G01N 33/86 422/63 |
| 7,126,676 | B2 | * | 10/2006 | Greco | G01N 33/4905 356/39 |
| 7,276,376 | B2 | * | 10/2007 | Katayama | G01N 33/4905 435/13 |
| 2003/0138962 | A1 | | 7/2003 | Katayama et al. | |
| 2008/0261254 | A1 | * | 10/2008 | Weyl | C12Q 1/56 435/13 |
| 2012/0288409 | A1 | * | 11/2012 | Inabe | G01N 21/51 422/82.05 |
| 2014/0255254 | A1 | * | 9/2014 | Yamaguchi | G01N 33/86 422/73 |

FOREIGN PATENT DOCUMENTS

| | | |
|---|---|---|
| JP | 2003-169700 A | 6/2003 |
| JP | 2008-209350 A | 9/2008 |
| JP | 2010-217059 A | 9/2010 |
| JP | 2010-261876 A | 11/2010 |

OTHER PUBLICATIONS

International Search Report of PCT/JP2014/057601.
Extended European Search Report received in corresponding European Application No. 14779633.8 dated Nov. 22, 2016.

* cited by examiner

AUTOMATIC COAGULATION ANALYZING APPARATUS AND ANALYZING METHOD

TECHNICAL FIELD

The present invention relates to an automatic analyzing apparatus that performs qualitative and quantitative analyses on a biological sample, such as blood or urine. More specifically, the invention relates to an automatic analyzing apparatus and an analyzing method that are involved in coagulation and hemostasis.

BACKGROUND ART

A blood coagulation examination is conducted for grasping a clinical condition of a coagulation-fibrinogenolysis system, diagnosing disseminated intravascular coagulation (DIC), confirming a therapeutic effect on thrombus, and diagnosing hemophilia. In particular, measurement of blood clotting time is an examination that directly checks whether a coagulation reaction generating fibrin correctly functions. The blood clotting time is prolonged in a case where there is a congenital or acquired abnormality.

Therefore, the blood coagulation examination is important as a means for checking, with screening, a bleeding tendency caused by various factors, such as abnormalities of a blood coagulation factor and a von Willebrand factor, hepatopathy, vitamin K deficiency, production of an inhibitor, and DIC.

Conventionally, the blood coagulation examination is conducted by visually capturing fibrin precipitation which is an end point of the blood coagulation reaction. Since the 1960s, an automatic analyzing apparatus developed for improvement of the processing number of specimens and high precision, has been used for an ordinary examination.

For example, an electric resistance detecting method, an optical method, and a mechanical method are mainly used for detecting fibrin precipitation by the automatic analyzing apparatus. The optical method (transmitted light detection, and scattered light detection) and the mechanical method (viscosity detection) that have excellent processing performance, have been mainly used.

In a clinical examination field, a measurement result of a patient specimen is required to be reported as soon as possible.

In relation to this, in measurement of a substance to be measured included in a sample by an automatic analyzing apparatus, the following calculating method has been known. A parameter in an approximate expression is calculated using a measurement value that varies with time. Then, the degree of convergence of reaction is determined in accordance with the degree of convergence of the parameter. A measurement value at the end of the reaction is calculated using a parameter at the time when it is determined that the reaction has converged (for example, refer to PTL 1).

As a result, measurement time can be changed for each specimen, and processing performance can be improved.

CITATION LIST

Patent Literature

PTL 1: JP 2010-261876 A

SUMMARY OF INVENTION

Technical Problem

In detection of fibrin precipitation in a blood coagulation examination, there are two pathways leading to fibrin precipitation, i.e., an endogenous pathway and an exogenous pathway. When a reaction pathway is abnormal, unstable behavior may occur.

Reasons for this include activation of various coagulation factors involved in each of the endogenous pathway and the exogenous pathway, and a step of the fibrin precipitation including multi-step reactions, such as a step for synthesizing a fibrin monomer from fibrinogen, and a step for starting to produce a fibrin polymer by an electrostatic bond of fibrin monomers.

As an example, when a high fibrinogen specimen of a patient to whom heparin has been administered is measured by the scattered light detection, activated partial thromboplastin time (APTT) sometimes becomes extremely short. It is thought that the specimen having been described above indicates a biphasic waveform caused by the coagulation reaction due to an extrinsic sthenic condition. After an observation of an early reaction in which an optical variation gradually varies from a lag phase, the optical variation due to an acceleration phase increases.

In this case, the method described in Patent Literature 1 continually calculates an approximate expression as needed, monitors a parameter varying with time, and completes measurement with convergence of the parameter. As a result, there is a problem that the measurement is forced to finish before a proper peak and clotting time is calculated erroneously.

An object of the present invention is to provide an automatic analyzing apparatus and an analyzing method that can accurately calculate clotting time.

Solution to Problem

In order to achieve the above object, the present invention includes: a detection unit configured to measure a coagulation index that indicates an amount of coagulated blood in a blood sample in which a reagent has been dispensed; a first curve fitting function configured to calculate, at a predetermined time interval, a parameter for an approximate curve of a coagulation curve by curve fitting, based on the measured coagulation index; an early reaction checking function configured to determine whether there is an early coagulation index change, based on the parameter for the approximate curve calculated at the predetermined time interval by the first curve fitting function, the early coagulation index change indicating a region in which the coagulation index increases immediately after the reagent is dispensed in the sample; and a clotting time calculation function configured to calculate a clotting time, based on whether there is the early coagulation index change.

Advantageous Effects of Invention

According to the present invention, clotting time can be accurately calculated. Problems, configurations, and effects other than those having been described above will be clearly given with the following embodiment.

DESCRIPTION OF EMBODIMENTS

A configuration and operation of an automatic analyzing apparatus 100 according to an embodiment of the present invention will be described with reference to FIGS. 1 to 10.

Figure 1:
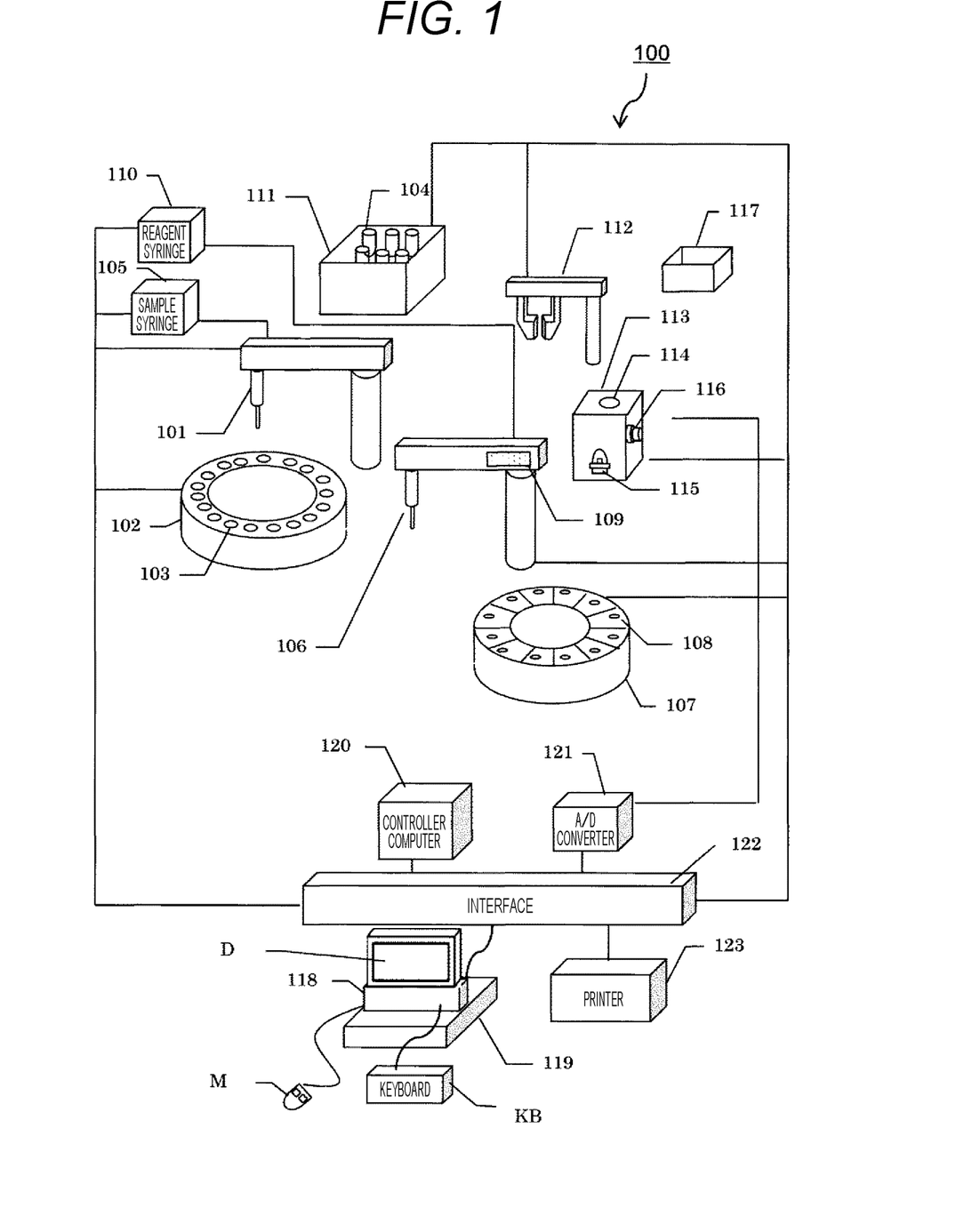
FIG. 1 is a configuration diagram of an automatic analyzing apparatus according to an embodiment of the present invention.

First, the entire configuration of the automatic analyzing apparatus 100 according to the embodiment of the present invention will be described with reference to FIG. 1. FIG. 1 is a configuration diagram of the automatic analyzing apparatus 100 according to the embodiment of the present invention.

The automatic analyzing apparatus 100 mainly includes a sample probe 101, a sample disk 102, a reagent probe 106, a reagent disc 107, a reaction vessel storage 111, a vessel carrier 112, a detection unit 113, a waste box 117, an operation computer 118, and a controller computer 120. The controller computer 120 includes an analysis operation controlling unit 120A that controls analysis operation and a data processing unit 120B that processes data.

The analysis operation controlling unit 120A in the controller computer 120 controls a series of operation including dispensations of a sample and a reagent, relocation of a reaction vessel, and disposal of the reaction vessel.

The sample probe 101 sucks a sample in a sample vessel 103 arranged in the sample disk 102 that rotates clockwise and counterclockwise, and discharges the sample to a reaction vessel 104 More specifically, the sample probe 101 performs sucking operation and discharge operation of the sample in accordance with operation of a sample syringe pump 105.

The reagent probe 106 sucks a reagent in a reagent vessel 108 arranged in the reagent disc 107, and discharges the reagent to the reaction vessel 104. More specifically, the reagent probe 106 performs sucking operation and discharge operation of the reagent in accordance with operation of a reagent syringe pump 110.

A reagent heater 109 is embedded in the reagent probe 106. The reagent sucked by the reagent probe 106 is heated to a suitable temperature (predetermined temperature) by the reagent heater 109.

The vessel carrier 112 carries and sets the reaction vessel 104. More specifically, the vessel carrier 112 rotates while holding the reaction vessel 104 so as to move and set the reaction vessel 104 from the reaction vessel storage 111 to a reaction vessel setting unit 114 of the detection unit 113.

The reaction vessel setting unit 114 includes a recess portion formed therein for setting the reaction vessel 104. The reaction vessel 104 can be inserted into the recess portion. Here, at least one reaction vessel setting unit 114 is provided. The automatic analyzing apparatus includes at least one detection unit 113.

Here, when the reagent probe 106 discharges the predetermined reagent to the reaction vessel 104 set in the reaction vessel setting unit 114, blood coagulation reaction begins. In other words, the blood coagulation reaction begins with the discharge operation for the reagent by the reagent probe 106 as a starting point.

An analysis item to be analyzed for each sample is input from the operation computer 118 to the controller computer 120 through a keyboard KB or an operation screen displayed on a displaying apparatus D. Note that the analysis item may be input by clicking, with a mouse M, the analysis item displayed on the displaying apparatus D. The controller computer 120 controls operation of the detection unit 113.

A light source 115 emits light to the reaction vessel 104. The light emitted from the light source 115 is scattered by a reaction solution in the reaction vessel 104.

The detection unit (optical sensor) 116 includes, for example, a photodiode. The detection unit 116 receives the scattered light scattered by the reaction solution in the reaction vessel 104, and performs a light/current conversion. Accordingly, the detection unit 116 outputs a photometric signal that indicates detected scattered light intensity.

An A/D converter 121 performs A/D conversion to the photometric signal. Then, the photometric signal is input into the controller computer 120 through an interface 122.

The data processing unit 120B in the controller computer 120 calculates clotting time, based on the photometric signal. The data processing unit 120B displays the calculated clotting time on the screen of the displaying apparatus D coupled to the operation computer 118, and stores the calculated clotting time in a hard disk 119 serving as a storage. Note that the data processing unit 120B may print the clotting time as a calculated result by a printer 123 through the interface 122.

The vessel carrier 112 holds and disposes the reaction vessel 104 in which the photometry has been completed, to the waste box 117.

Figure 2:
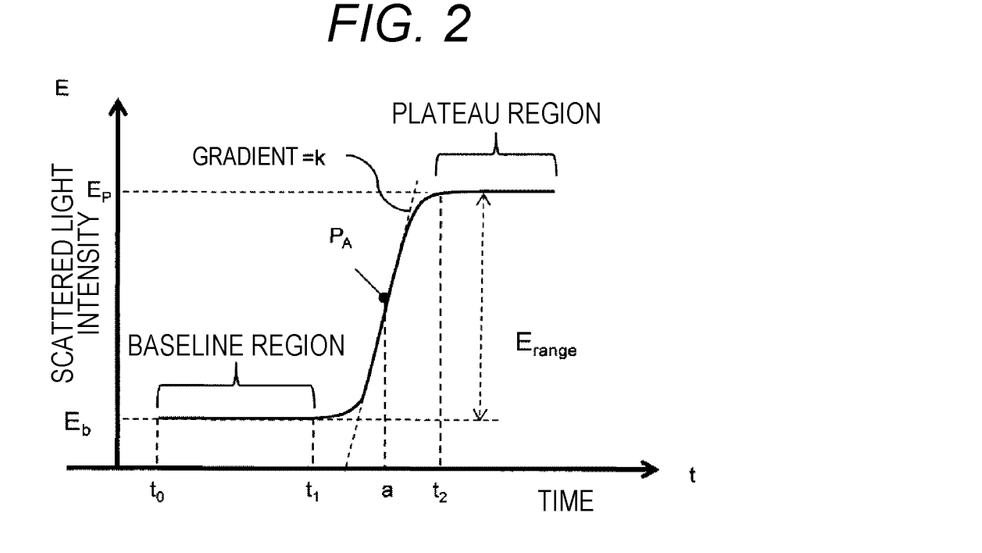
FIG. 2 is a schematic graphical representation of an ideal coagulation curve in a case where an analysis item is APTT in the automatic analyzing apparatus according to the embodiment of the present invention.

Next, in a case where the analysis item is APTT in the automatic analyzing apparatus 100 according to the embodiment of the present invention, an ideal coagulation curve will be described with reference to FIG. 2. FIG. 2 is a schematic graphical representation of the ideal coagulation curve in a case where the analysis item is APTT in the automatic analyzing apparatus 100 according to the embodiment of the present invention. In FIG. 2, the vertical axis represents scattered light intensity E, and the horizontal axis represents time t.

In FIG. 2, the scattered light intensity E becomes a constant minimal value $E_b$ from the beginning timing of measurement $t=t_0$ to timing $t=t_1$. Meanwhile, the scattered light intensity E becomes a constant maximal value $E_P$ at and after timing $t=t_2$.

In the ideal coagulation curve, a region in which the scattered light intensity E becomes the constant minimal value $E_b$ is called a baseline region. A region in which the scattered light intensity E becomes the constant maximal value $E_P$ is called a plateau region. A scattered light variation $E_{range}$ represents the difference between the maximal value $E_P$ and the minimal value $E_b$ of the scattered light intensity E.

The controller computer 120 performs curve fitting to measured data of the scattered light intensity E so as to determine an approximate curve that indicates the coagulation curve. Detailed operation of the controller computer 120 will be described later with reference to FIG. 7.

Here, the curve fitting is defined as acquiring a curve that substantially fits the measured data. Regression analysis is typically used for the curve fitting. In the curve fitting, predetermined iteration processing is performed in order to determine a parameter with respect to a function including one or more parameters.

When the regression analysis is used to acquire a curve, the curve does not necessarily pass through data points (points indicating measurement values). In order to determine a parameter that minimizes a distance between the curve and the data point group, the regression analysis performs predetermined iteration calculation processing so as to search for and determine an optimum parameter.

Note that the curve acquired by the curve fitting is defined as an approximate curve. The parameter determined by the curve fitting is defined as an approximate parameter. An expression acquired by substituting the approximate parameter into the original function is defined as an approximate expression.

The coagulation curve indicates a sigmoid shape. Therefore, for example, a sigmoid curve represented by the following expression (1) can be used as an approximate function.

[Expression 1]

$$E(t) = \frac{E_{range}}{1 + \exp\left(\frac{t-a}{k}\right)} + E_b \quad (1)$$

Here, a parameter a represents time t at an inflection point $P_A$ illustrated in FIG. 2. A parameter k represents a gradient of the curve in a region interposed between the baseline region and the plateau region (the degree of a gradient of a leading edge portion in the coagulation curve).

Curve fitting using the approximate function represented by expression (1) determines four parameters $E_{range}$, $E_b$, a, and k.

Actually, however, the sigmoid curve that fits measurement values is often not necessarily in point symmetry. Therefore, the following expression (2) including a correction parameter b of point symmetry (parameter for correction) is used in the present embodiment.

[Expression 2]

$$E(t) = \frac{E_{range}}{\left\{1 + \exp\left(\frac{t-a}{k}\right)\right\}^b} + E_b \quad (2)$$

Here, an approximate curve is represented by the following expression (3), where $E_{range}^{(1)-1}$, $a^{(1)-1}$, $b^{(1)-1}$, $k^{(1)-1}$ and $E_b^{(1)-1}$ are parameters calculated by the curve fitting.

[Expression 3]

$$E = \frac{E_{range}^{(I)-1}}{1 + \exp\left(\frac{t - a^{(I)-1}}{k^{(I)-1}}\right)^{b^{(I)-1}}} + E_b^{(I)-1} \quad (3)$$

Figure 3:
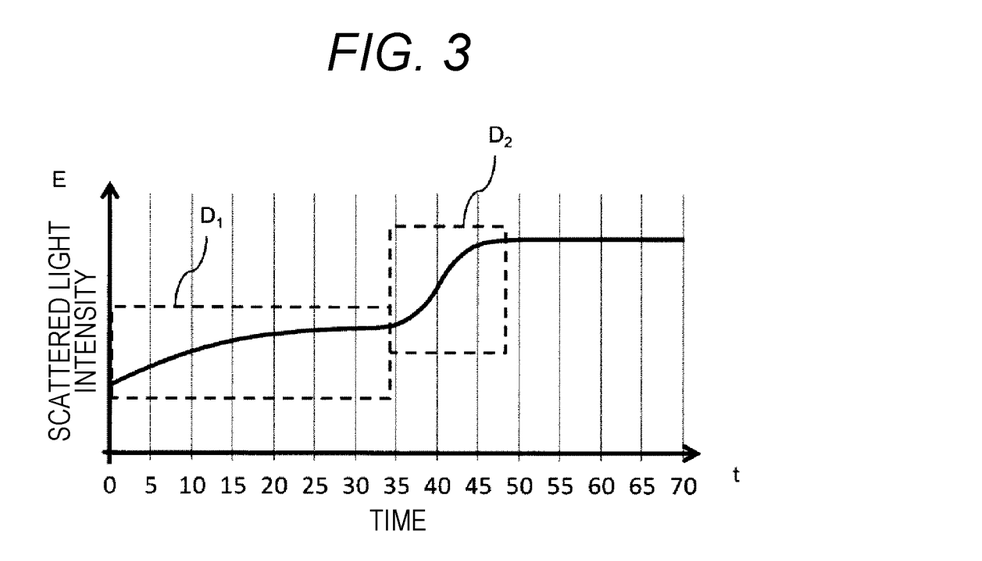
FIG. 3 is a graphical representation of an exemplary actual coagulation curve in a case where the analysis item is APTT in the automatic analyzing apparatus according to the embodiment of the present invention.

Next, an exemplary actual coagulation curve in a case where the analysis item is APTT in the automatic analyzing apparatus 100 according to the embodiment of the present invention will be described with reference to FIG. 3. FIG. 3 is a graphical representation of an exemplary actual coagulation curve in a case where the analysis item is APTT in the automatic analyzing apparatus 100 according to the embodiment of the present invention. In FIG. 3, the vertical axis represents scattered light intensity E, and the horizontal axis represents time t.

The coagulation curve illustrated in FIG. 3 indicates a biphasic waveform due to an abnormal reaction pathway. In FIG. 3, a lag phase $D_1$ is observed as a first waveform immediately after measurement is started. After that, an acceleration phase $D_2$ is observed as a second waveform.

Here, in the coagulation curve, the lag phase represents a portion in which the scattered light intensity E increases immediately after a reagent is dispensed in a sample. In other words, in the lag phase, time differentiation of the scattered light intensity E becomes positive (dE/dt>0). Curve fitting is performed in this portion so that the approximate parameters $E_{range} \neq 0$ and $k \neq 0$ are satisfied.

In the coagulation curve, the acceleration phase represents a portion in which the scattered light intensity E increases after the lag phase. In other words, in the acceleration phase, time differentiation of the scattered light intensity E becomes positive (dE/dt>0). In FIG. 3, the time differentiation of the scattered light intensity E in the acceleration phase $D_2$ is larger than that of the scattered light intensity E in the lag phase $D_1$.

Figure 4A:
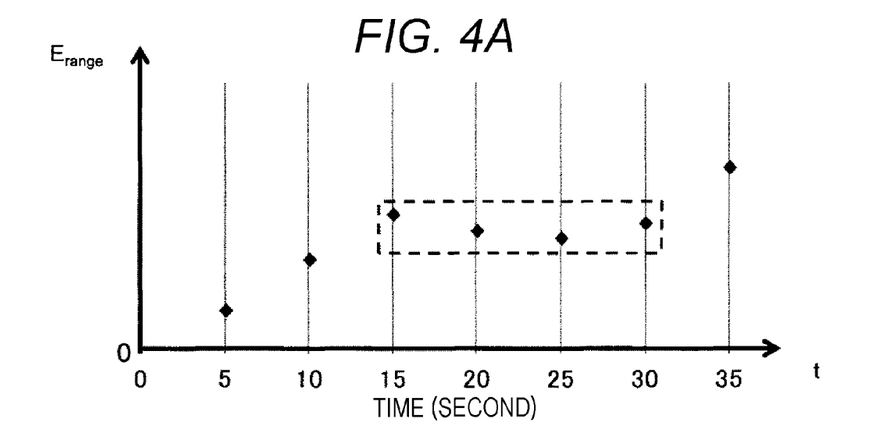
FIG. 4A is a graphical representation of a result in which an approximate parameter $E_{range}$ in a lag phase illustrated in FIG. 3 is calculated every five seconds and plotted.
Figure 4B:
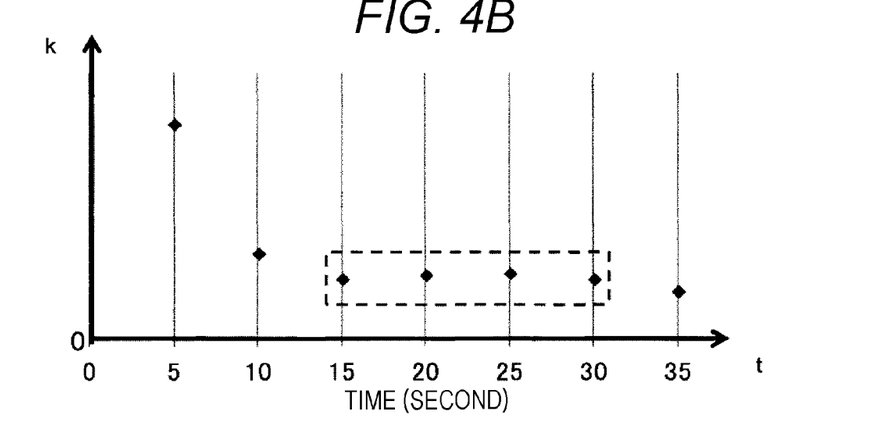
FIG. 4B is a graphical representation of a result in which an approximate parameter k in the lag phase illustrated in FIG. 3 is calculated every five seconds and plotted.

Next, transitions of the approximate parameters in the lag phase $D_1$ illustrated in FIG. 3 will be described with reference to FIG. 4. FIG. 4 illustrates graphical representations of the transitions of the approximate parameters in the lag phase $D_1$ illustrated in FIG. 3.

FIG. 4(A) is a graphical representation of a result in which the approximate parameter $E_{range}$ in the lag phase $D_1$ illustrated in FIG. 3 is calculated every five seconds and plotted. In FIG. 4(A), the vertical axis represents the approximate parameter $E_{range}$, and the horizontal axis represents time t. Note that a time range satisfies $0 \leq t \leq 35$. In FIG. 4(A), the approximate parameter $E_{range}$ results in a substantially constant value from around 15 to 30 seconds.

Meanwhile, FIG. 4(B) is a graphical representation of a result in which the approximate parameter k in the lag phase $D_1$ illustrated in FIG. 3 is calculated every five seconds and plotted. In FIG. 4(B), the vertical axis represents the approximate parameter k, and the horizontal axis represents time t. Note that a time range satisfies 0≤t≤35. In FIG. 4(B), the approximate parameter k results in a substantially constant value from around 15 to 30 seconds.

Figure 5A:
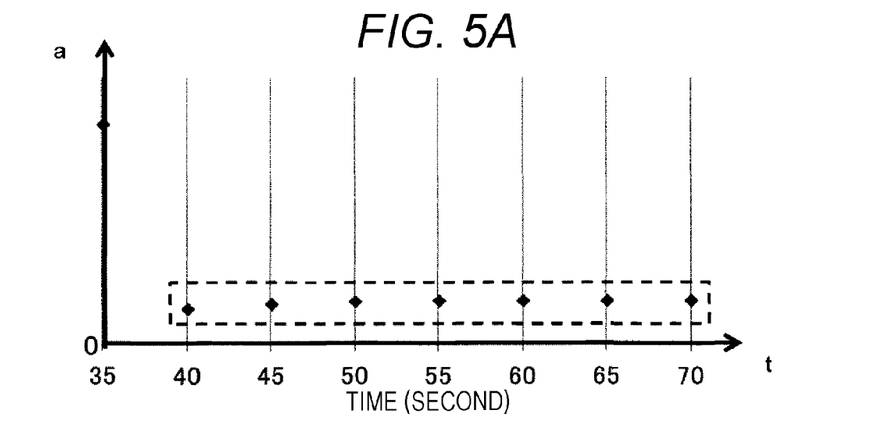
FIG. 5A is a graphical representation of a result in which an approximate parameter a in and after an acceleration phase illustrated in FIG. 3 is calculated every five seconds and plotted.
Figure 5B:
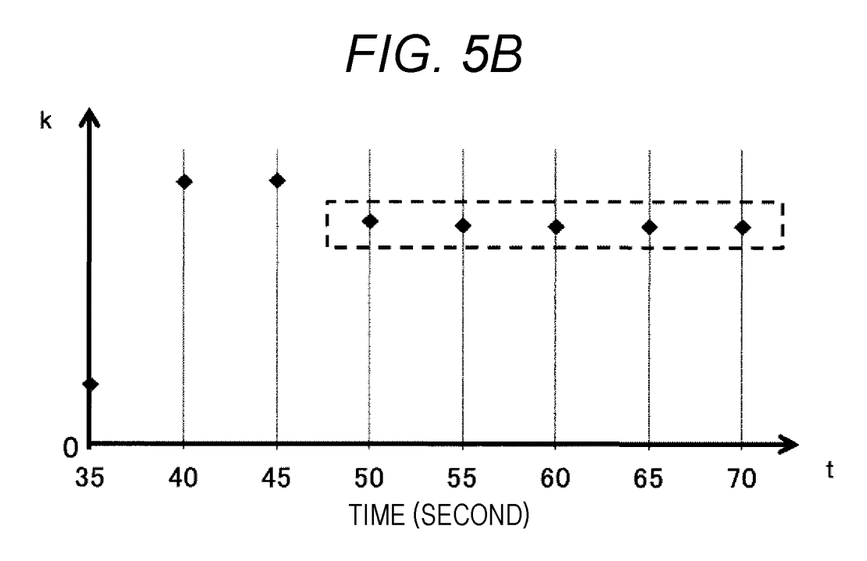
FIG. 5B is a graphical representation of a result in which an approximate parameter k in and after the acceleration phase illustrated in FIG. 3 is calculated every five seconds and plotted.

Next, transitions of the approximate parameters in and after the acceleration phase $D_2$ illustrated in FIG. 3 will be described with reference to FIG. 5. FIG. 5 illustrates graphical representations of the transitions of the approximate parameters in and after the acceleration phase $D_2$ illustrated in FIG. 3.

FIG. 5(A) is a graphical representation of a result in which the approximate parameter a in and after the acceleration phase $D_2$ illustrated in FIG. 3 is calculated every five seconds and plotted. In FIG. 5(A), the vertical axis represents the approximate parameter a, and the horizontal axis represents time t. Note that, in FIG. 5(A), a time range satisfies t≥35.

There is the inflection point $P_A$ illustrated in FIG. 2 in the middle of the sigmoid curve. The approximate parameter a that indicates a value of time t at the inflection point $P_A$ converges first. In an example in FIG. 5(A), the approximate parameter a converges to a constant value after approximately 40 seconds from the beginning of the measurement.

FIG. 5(B) is a graphical representation of a result in which the approximate parameter k in and after the acceleration phase $D_2$ illustrated in FIG. 3 is calculated every five seconds and plotted. In FIG. 5(B), the vertical axis represents the approximate parameter k, and the horizontal axis represents time t. Note that, in FIG. 5(B), a time range satisfies t≥35.

When a curve portion corresponding to the acceleration phase $D_2$ illustrated in FIG. 3 is finished, the approximate parameter k converges. In an example in FIG. 5(B), the approximate parameter k converges to a constant value after approximately 50 seconds.

Figure 6:
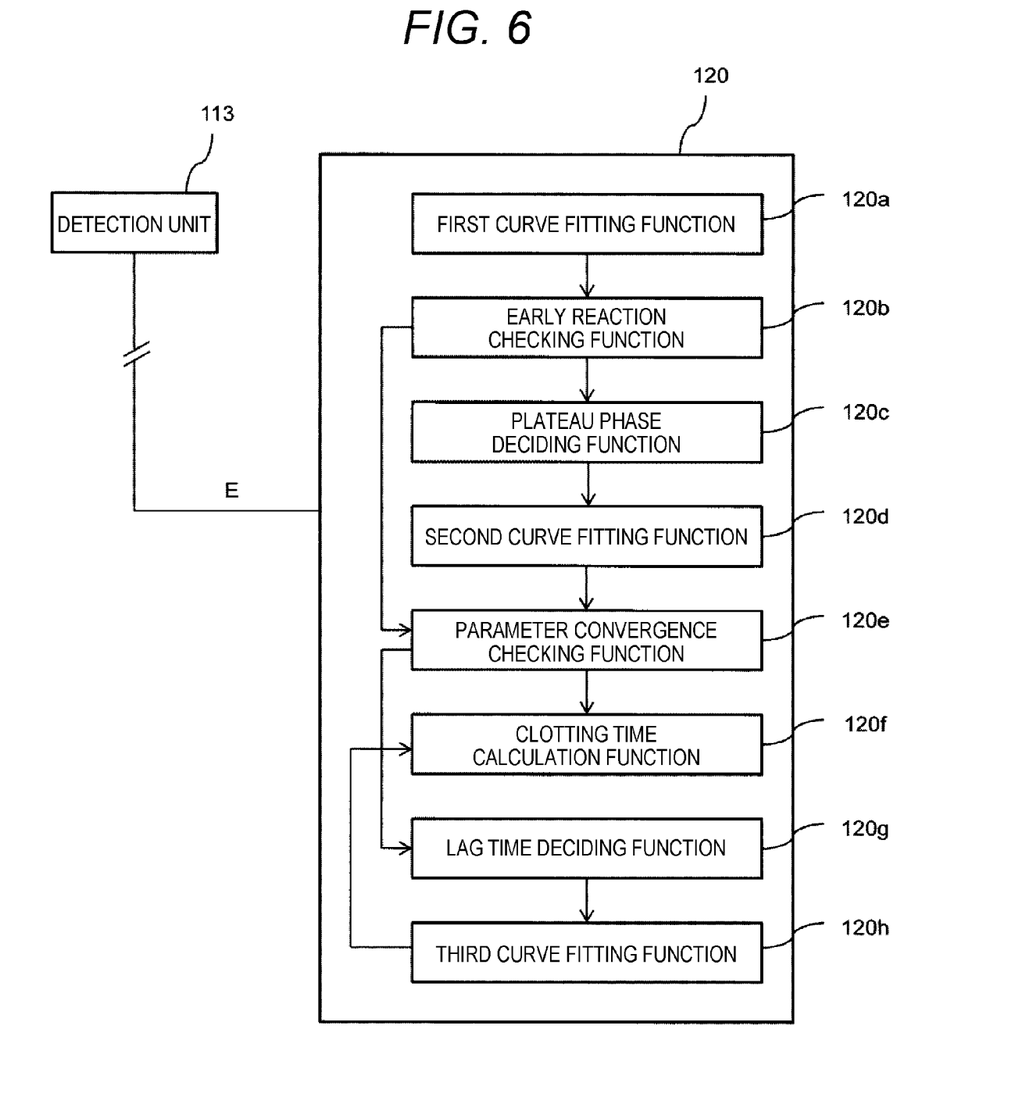
FIG. 6 is a block diagram of functions of a controller computer used in the automatic analyzing apparatus according to the embodiment of the present invention.

Next, functions of the controller computer 120 used for the automatic analyzing apparatus 100 according to the embodiment of the present invention will be described with reference to FIG. 6. FIG. 6 is a block diagram of the functions of the controller computer 120 used for the automatic analyzing apparatus 100 according to the embodiment of the present invention.

The data processing unit 120B in the controller computer 120 includes a first curve fitting function 120B-a, an early reaction checking function 120B-b, a plateau phase deciding function 120B-c, a second curve fitting function 120B-d, a parameter convergence checking function 120B-e, a clotting time calculation function 120B-f, a lag time deciding function 120B-g, and a third curve fitting function 120B-h.

The first curve fitting function 120B-a performs curve fitting to measurement data so as to calculate an approximate parameter.

The early reaction checking function 120B-b determines whether there is a lag phase, based on the calculated approximate parameter.

The plateau phase deciding function 120B-c determines whether a first waveform is completed in the biphasic waveform when there is the lag phase.

When the first waveform is completed, the second curve fitting function 120B-d performs curve fitting to measurement data in a second waveform, not in the first waveform, so as to calculate an approximate parameter.

The parameter convergence checking function 120B-e determines whether the approximate parameter has converged.

The clotting time calculation function 120B-f calculates clotting time based on an approximate function in which the approximate parameter is substituted.

When there is no lag phase, the lag time deciding function 120B-g determines, based on the measurement data, the beginning point of lag time from which an optical change begins.

When there is no lag phase, the third curve fitting function 120B-h performs curve fitting from the beginning point of the lag time to measurement end point so as to calculate an approximate parameter.

Figure 7:
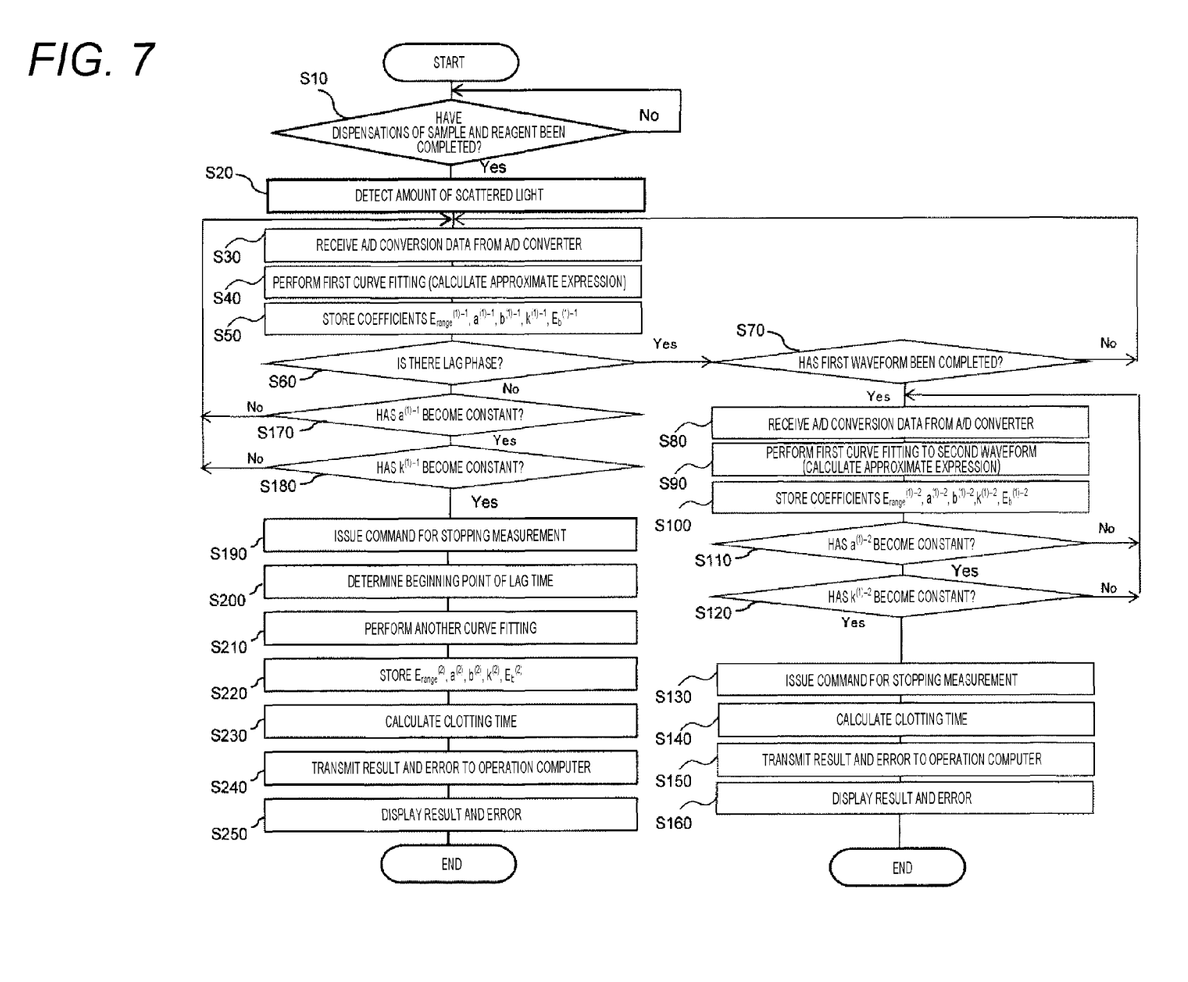
FIG. 7 is a flowchart of operation of the automatic analyzing apparatus according to the embodiment of the present invention.

Note that detailed descriptions of these functions will be described later with reference to FIG. 7.

Next, operation of the automatic analyzing apparatus 100 according to the embodiment of the present invention will be described with reference to FIG. 7. FIG. 7 is a flowchart of the operation of the automatic analyzing apparatus 100 according to the embodiment of the present invention.

An example where the analysis item (examination item) is APTT and a coagulation reaction includes a biphasic waveform will be described below. Note that the analysis item is not limited to the APTT.

More specifically, it is assumed that a biphasic waveform proceeds in accordance with the coagulation curve illustrated in FIG. 3 and the approximate parameters converge as illustrated in FIGS. 4 and 5.

First, upon completion of dispensations of a reagent and a sample into a reaction vessel 104 set in the reaction vessel setting unit 114 (step S10; Yes), the detection unit 113 successively detects (measures) the scattered light intensity E that indicates an amount of scattered light from the reaction vessel 104 (step S20).

The A/D converter 121 collects a photometric signal (light/current conversion data) that indicates the scattered light intensity E detected by the detection unit 113 in each constant period (S seconds) so as to perform A/D conversion to the photometric signal.

The first curve fitting function 120B-a receives A/D conversion data (photometric signal to which the A/D conversion is performed) from the A/D converter 121 (step S30).

The first curve fitting function 120B-a performs, in a constant period, curve fitting to the A/D conversion data so as to calculate parameters of an approximate curve (step S40).

Note that as the period of the curve fitting is shorter, the measurement completion can be determined with a higher resolution However, when the number of curve fitting processing increases, a load of the controller computer 120 increases. Therefore, the period of the curve fitting may not be equal to the conversion period S seconds of the A/D converter 121.

The period of the curve fitting may be changed for each analysis item. The same period of the curve fitting may be used for all or a part of the analysis items.

Furthermore, in order to reduce the load of the controller computer 120, a part of the successively collected measurement data may be thinned. In other words, for example, even when the measurement is performed every 0.1 seconds, data is thinned every one second upon the curve fitting so that the number of the data can be reduced to one tenth thereof and the load of the controller computer 120 can be reduced.

Referring back to FIG. 7, the first curve fitting function 120B-a stores, in the hard disk 119, approximate parameters $E_{range}^{(1)-1}$, $a^{(1)-1}$, $b^{(1)-1}$, $k^{(1)-1}$, and $E_b^{(1)-1}$ calculated by the curve fitting (step S50).

In this case, each time the approximate parameters are calculated, the first curve fitting function 120B-a stores the respective parameter values. Accordingly, the first curve fitting function 120B-a stores change of each of the approximate parameters over time so as to monitor the approximate parameters that vary with time.

As in the following description, the early reaction checking function 120B-b checks whether there is the lag phase, and appropriately selects (changes) processing that calculates clotting time in accordance with the presence/absence of the lag phase. This point is one of definitive differences from a conventional example.

The early reaction checking function 120B-b monitors the approximate parameters $E_{range}$ and k so as to check whether there is the lag phase (step S60). More specifically, the early reaction checking function 120B-b determines that there is the lag phase when $E_{range} \neq 0$ or $k \neq 0$ is satisfied.

In the biphasic waveform illustrated in FIG. 3, a scattered light variation is observed as the lag phase before approximately t=35 seconds. The approximate curve becomes a gentle curve. When curve fitting is performed in this time range, neither the approximate parameter $E_{range}$ nor the approximate parameter k becomes zero.

When there is the lag phase, a reaction includes the biphasic waveform. In order to avoid completing the measurement by mistake after the first waveform, it is necessary to carefully determine the end point of the lag time. Thus, whether there is the lag phase is determined. Then, when there is the lag phase, it is necessary to first check completion of the first waveform.

The plateau phase deciding function 120B-c monitors the approximate parameter $E_{range}$ and the approximate parameter k so as to determine whether the first waveform has been completed (step S70).

More specifically, when the approximate parameter $E_{range}$ and the approximate parameter k become constant, the plateau phase deciding function 120B-c determines that the first waveform has been completed. Here, the end point of a period during which the approximate parameter $E_{range}$ and the approximate parameter k are constant is defined as the completion of the first waveform.

For example, the approximate parameter $E_{range}$ remains constant from 15 to 30 seconds in FIG. 4(A). The approximate parameter k remains constant from 15 to 30 seconds in FIG. 4(B). Therefore, the plateau phase deciding function 120B-c determines that the first waveform has been completed at t=30 seconds.

In a case where the completion of the first waveform is determined (step S70; Yes), the second curve fitting function 120B-d receives A/D conversion data from the A/D converter 121 (step S80).

The second curve fitting function 120B-d performs curve fitting to the A/D conversion data in a constant period using expression (2) so as to calculate parameters of an approximate curve (step S90).

The second curve fitting function 120B-d stores, in the hard disk 119, approximate parameters $E_{range}^{(1)-2}$, $a^{(1)-2}$, $b^{(1)-2}$, $k^{(1)-2}$, and $E_b^{(1)-2}$ calculated by the curve fitting (step S100).

Here, data to be subjected to the fitting includes only measurement data in the second waveform, not including the first waveform.

The parameter convergence checking function 120B-e completes the measurement upon convergence of the approximate parameters a and k.

More specifically, the parameter convergence checking function 120B-e determines whether the approximate parameter $a^{(1)-2}$ has converged and remains constant (step S110).

In a case where the approximate parameter $a^{(1)-2}$ becomes constant (step S110; Yes), the parameter convergence checking function 120B-e determines whether the approximate parameter $k^{(1)-2}$ has converged and remains constant (step S120).

When the parameter convergence checking function 120B-e determines that both of the approximate parameters $a^{(1)-2}$ and $k^{(1)-2}$ have converged (step S110; Yes, step S120; Yes), the analysis operation controlling unit 120A of the controller computer 120 that has received a result from the parameter convergence checking function 120B-e issues an instruction for completing detection of the amount of scattered light of a specimen for which the measurement is to be completed (step S130).

The clotting time calculation function 120B-f substitutes, into expression (2), the approximate parameters $E_{range}^{(1)-2}$, $a^{(1)-2}$, $b^{(1)-2}$, $k^{(1)-2}$, and $E_b^{(1)-2}$, which correspond to a peak of the second waveform, stored upon the completion of the measurement. Then, the clotting time calculation function 120B-f calculates clotting time (step S140).

Methods for calculating the clotting time include, for example, (i) a percentile method, (ii) a first derivation method, (iii) a quadratic differential method, and (iv) an inflection point method.

The percentile method is as follows. A constant rate in the scattered light variation from the beginning to the end of the reaction is set as a threshold. The clotting time calculation function 120B-f determines, as the clotting time, time exceeding the threshold. For example, when the threshold is 50% of the scattered light variation, an expression that represents $E_{range}^{(1)-2} \times 0.5 + E_b =$ the right side of expression (2) is solved so that the clotting time t is calculated.

The first derivation method is as follows. Time when a differential value (scattered light variation) of the amount of the scattered light becomes maximal, is defined as the clotting time. An approximate expression acquired by substituting $E_{range}^{(1)-2}$, $a^{(1)-2}$, $b^{(1)-2}$, $k^{(1)-2}$, and $E_b^{(1)-2}$ into expression (2) is linearly differentiated so that the maximum value is calculated.

The quadratic differential method is as follows. Time when a quadratic differential value of the amount of the scattered light becomes maximal, is defined as the clotting time. A quadratic differentiation is performed to an approximate expression acquired by substituting $E_{range}^{(1)-2}$, $a^{(1)-2}$, $b^{(1)-2}$, $k^{(1)-2}$, and $E_b^{(1)-2}$ into expression (2). Then, the resultant maximum value is calculated. In the inflection point method, $a^{(1)-2}$ without any change is defined as the clotting time.

The data processing unit 120B in the controller computer 120 transmits the calculated clotting time to the operation computer 118 (step S150) so that the result is displayed on the displaying apparatus D (step S160).

The biphasic waveform is an abnormal reaction. Thus, an error is displayed in order to indicate that the clotting time is calculated from the second waveform.

As described above, according to the present embodiment, even when the coagulation reaction includes the biphasic waveform, the clotting time can be calculated and a user can be notified of abnormality.

(Modification 1)

Another method for determining whether there is a lag phase may include using measurement data without any change. When a threshold of a scattered light variation is exceeded, it may be determined that there is the lag phase.

In this case, the data processing unit 120b in the controller computer 120 may determine that there is the lag phase when a difference between scattered light intensity $E_0$ at timing when measurement is started and the latest measured scattered light intensity E exceeds a predetermined threshold.

(Modification 2)

Alternatively, determination as to whether there is the lag phase is not performed immediately after the start of measurement. An approximate parameter is continuously monitored until a predetermined minimal measurement time. Whether there is the lag phase may be determined after confirming occurrence of an outlier after temporary convergence of the approximate parameter.

In other words, when there is the lag phase, time when a first waveform is completed comes earlier than a proper peak. Therefore, a minimal measurement time may be set for each analysis item in advance.

Figure 8A:
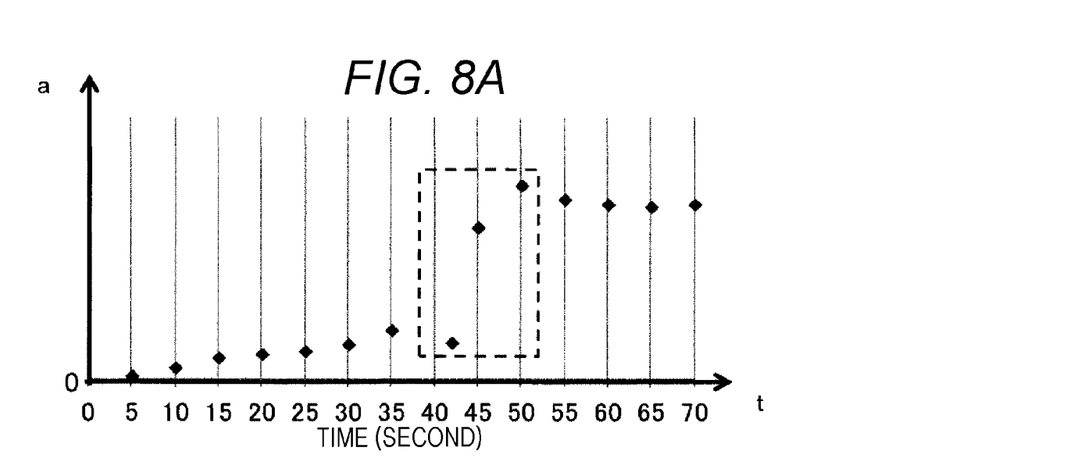
FIG. 8A is a graphical representation of a transition of an approximate parameter a in a modification.
Figure 8B:
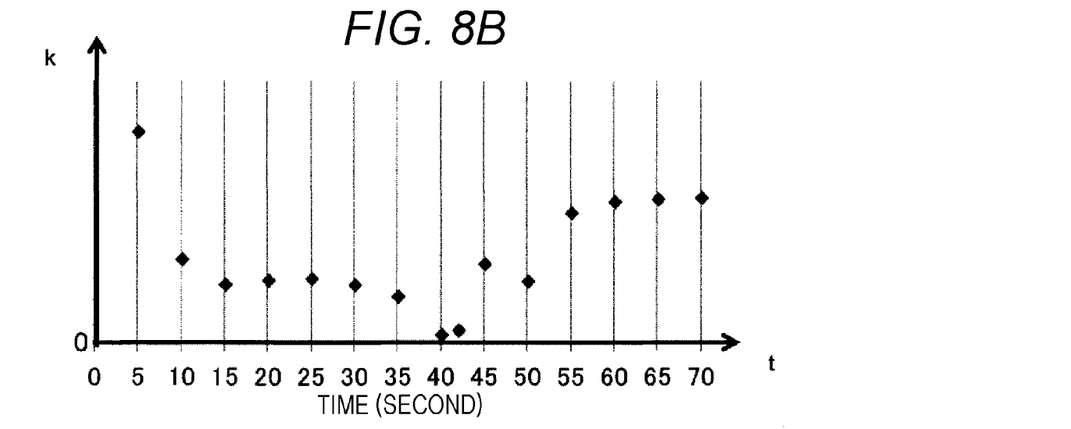
FIG. 8B is a graphical representation of a transition of an approximate parameter k in the modification.

Specific examples are illustrated in FIG. 8. Specific values may be different from those in the embodiment. FIG. 8 illustrates graphical representations of transitions of approximate parameters according to the present modification. For example, when the minimal measurement time is set to 50 seconds, a and k become ubstantially constant from around 15 to 30 seconds in FIGS. 8(A) and (B). Thus, it is suspected that the first waveform has been completed. However, the measurement is continued until the minimal measurement time.

After that, as an error value, a rapid change of a is observed from around 40 seconds when the first waveform is completed. In this case, it is determined that there is the lag phase.

Next, another example of an actual coagulation curve in a case where the analysis item is APTT in the automatic analyzing apparatus 100 according to the embodiment of the present invention, will be described with reference to FIG. 9.

Figure 9:
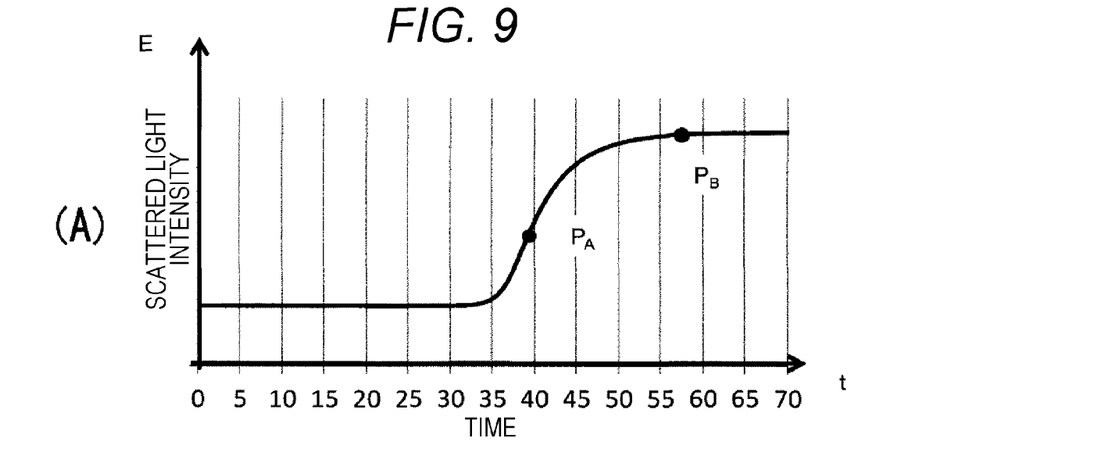
FIG. 9 is a graphical representation of another exemplary actual coagulation curve in a case where the analysis item is APTT in the automatic analyzing apparatus according to the embodiment of the present invention.

FIG. 9 is a graphical representation of another exemplary actual coagulation curve in a case where the analysis item is APTT in the automatic analyzing apparatus 100 according to the embodiment of the present invention.

Note that the vertical axis represents scattered light intensity E, and the horizontal axis represent time t. An inflection point is denoted with $P_A$. A measurement completion point indicating a point at which the measurement is completed, is denoted with $P_B$.

In FIG. 9, no scattered light variation is observed immediately after addition of a reagent when compared with FIG. 3.

An approximate curve becomes a straight line indicating E=0 before around t=35 seconds. When curve fitting is performed in this time range, $E_{range}$=0 and k=0 are satisfied.

Figure 10A:
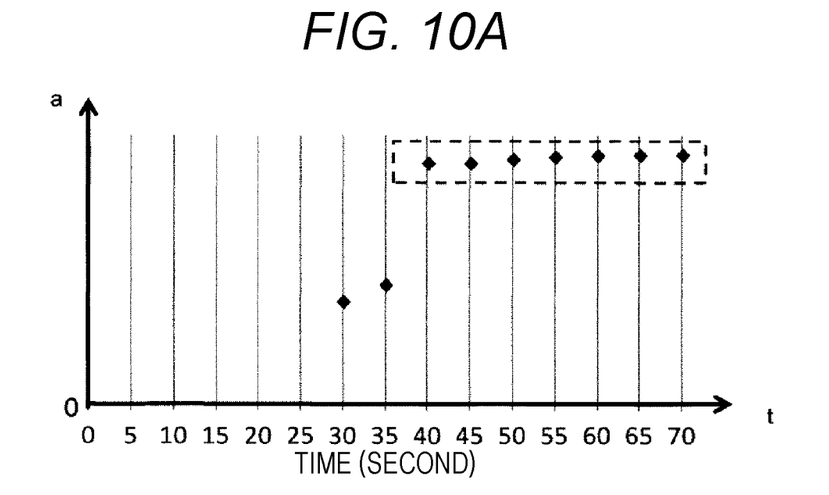
FIG. 10A is a graphical representation of a result in which a parameter a in the coagulation curve illustrated in FIG. 9 is calculated every five seconds and plotted.
Figure 10B:
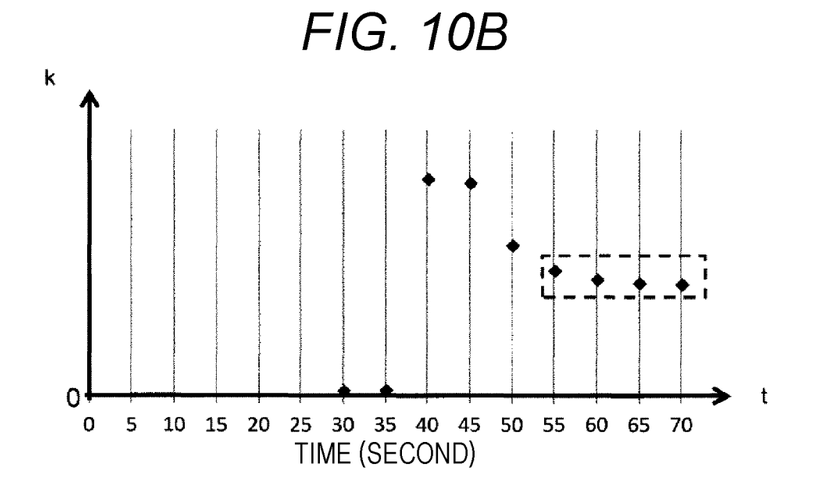
FIG. 10B is a graphical representation of a result in which a parameter k in the coagulation curve illustrated in FIG. 9 is calculated every five seconds and plotted.

Next, transitions of the approximate parameters in the coagulation curve illustrated in FIG. 9 will be described with reference to FIG. 10. FIG. 10 illustrates graphical representations of the transitions of the approximate parameters in the coagulation curve illustrated in FIG. 9.

FIG. 10(A) is a graphical representation of a result in which the approximate parameter a in the coagulation curve illustrated in FIG. 9 is calculated every five seconds and plotted. In FIG. 10(A), the vertical axis represents the approximate parameter a, and the horizontal axis represents time t.

In an example of FIG. 10(A), the approximate parameter a converges to a constant value at and after an inflection point $P_A$ (at and after around 40 seconds after the measurement is started) illustrated in FIG. 9.

FIG. 10(B) is a graphical representation of a result in which the parameter k in the coagulation curve illustrated in FIG. 9 is calculated every five seconds and plotted. In FIG. 10(B), the vertical axis represents the approximate parameter k, and the horizontal axis represents time t.

In an example of FIG. 10(B), the approximate parameter k converges to a constant value at and after $P_B$ (at and after around 55 seconds after the measurement is started) illustrated in FIG. 9.

Next, operation of the automatic analyzing apparatus 100 according to the embodiment of the present invention will be described with reference to FIG. 7.

A processing flow that calculates clotting time for a specimen without the lag phase (in and after step S170 in FIG. 7) will be described below.

More specifically, it is assumed that a reaction proceeds in accordance with the coagulation curve illustrated in FIG. 9, and the approximate parameters converge as illustrated in FIG. 10.

The parameter convergence checking function 120B-e determines whether the approximate parameter $a^{(1)-1}$ has converged and remains constant (step S170).

When the approximate parameter $a^{(1)-1}$ becomes constant (step S170; Yes), the parameter convergence checking function 120B-e determines whether the approximate parameter $k^{(1)-1}$ has converged and remains constant (step S180).

The analysis operation controlling unit 120A in a controller computer 120 reflects the result from the parameter convergence checking function 120B-e. When an approximate parameter $k^{(1)-1}$ variation is in a constant range, namely, the approximate parameter $k^{(1)-1}$ becomes constant (step S180; Yes), the analysis operation controlling unit 120A completes the specimen measurement to be completed and issues an instruction for completing detection of the amount of scattered light (step S190).

A second point of definitive differences between the present invention and the conventional method is that the approximate parameters determined at the point of the measurement completion are not used without any change. As in the following description, the lag time deciding function 120B-g determines the beginning point of lag time. The third curve fitting function 120B-h performs curve fitting. Here, the beginning point of the lag time means a point from which an optical change begins.

A coagulation examination has the following characteristic. Since measurement is started immediately after a reagent is added, a liquid surface is unstable immediately after the measurement is started. Therefore, noise may easily occur. When an approximate curve in a lag phase becomes inaccurate due to the noise, an error sometimes occurs in the clotting time.

Therefore, in order to more accurately calculate the clotting time, it is important to arrange so as not to use data including a large amount of noise immediately after the lag time begins.

In particular, an S/N ratio decreases in a specimen of low fibrinogen plasma. Thus, an effect of noise is severe. For example, the approximate parameters $E_{range}$ and k can be used as a method for defining the beginning point of the lag time.

In the coagulation curve for the specimen without the lag phase, $E_{range}$=0 and k=0 are satisfied before the scattered light variation begins. A last point that satisfies $E_{range}$=0 and k=0 can thus be defined as the beginning point of the lag time. As another method for determining the beginning point of the lag time and the end point thereof, in the coagulation curve for the specimen without the lag phase, a differential value in the approximate expression acquired by substituting approximate parameters $E_{range}^{(1)-2}$, $a^{(1)-2}$, $b^{(1)-2}$, $k^{(1)-2}$, and $E_b^{(1)-2}$ into expression (2) can be also used. In other words, a region including no scattered light variation can be defined as before the beginning point of the lag time and at and after the reaction completion.

Furthermore, an expanding example of the method for determining the beginning point of the lag time and the end point thereof includes, for example, a case where a quadratic differential value of the amount of the scattered light becomes zero and another case where a quadratic differential value of an integrated value of the amount of the scattered light becomes zero.

Referring back to FIG. 7, the third curve fitting function 120B-h performs curve fitting from just before the beginning point of the lag time to a measurement end point (step S210), determines approximate parameters $E_{range}^{(2)}$, $a^{(2)}$, $b^{(2)}$, $k^{(2)}$, and $E_b^{(2)}$, and stores the approximate parameters in the hard disk 119 (step S220).

The clotting time calculation function 120B-f substitutes the determined parameters into expression (2) so as to calculate the clotting time (step S230). Note that the processing in step S230 is similar to that in step S140.

The clotting time calculation function 120B-f transmits the calculated clotting time to the operation computer 118 (step S240) so that the result is displayed on the displaying apparatus D (step S250).

As described above, according to the present embodiment, the clotting time for the specimen without the lag phase can be accurately calculated. This is because, in a case where there is no lag phase, the data including a large amount of noise just after the beginning of the lag time is not used for a coagulation calculation.

The present invention is not limited to the above embodiment, and includes various modifications. For example, the above embodiment has been described in detail in order to easily understand the present invention. The present invention is not necessarily limited to including all the configurations having been described above. A part of a configuration in one embodiment can be replaced with a configuration in another embodiment. In addition, a configuration in one embodiment can be added to a configuration in another embodiment. With respect to a part of the configuration in each of the embodiments, additions, deletions, and replacements of the other configurations may be made.

In the above embodiment, whether there is the lag phase is determined based on the measurement data of the scattered light intensity E. However, the measurement data may be any of coagulation indices that indicate an amount of coagulated blood.

In the above embodiment, an example in which the approximate parameter $E_{range}$, the approximate parameter k, and the approximate parameter are used for determining completion of the first waveform and the second waveform, has been introduced. Any of the parameters may be used or combined as long as at least one parameter among the parameters is monitored.

In the above embodiment, the controller computer 120 performs calculation processing of the clotting time. The A/D conversion data received by the controller computer 120 may be transmitted to the operation computer 118 through the interface 122. The operation computer 118 may perform the processing.

As illustrated in Table 1, other than the sigmoid curve, for example, a logistic curve represented by expression (4), a Gompertz curve represented by expression (5), a Hill curve represented by expression (6), and a Chapman curve represented by expression (7) can be used for an approximate function. In particular, in the above embodiment, a clotting time analysis method in the detection of the scattered light has been described. The detecting method may include the transmitted light detection and the viscosity detection. In this case, a similar expression can be used.

As specific examples, the expressions as illustrated in Table 1 have been given. However, another similar expression that substantially best fits the coagulation curve is preferably selected. In this case, the following method may be used. Whether there is the lag phase (or viscosity change) is determined. When there is the lag phase (or the viscosity change), fitting is performed again in the second waveform after completion of the first waveform is confirmed. Then, the parameters varying with time are monitored and the completion of the reaction is determined. After that, the clotting time is calculated.

Since an ideal reaction curve shape of the coagulation reaction depends on items, an appropriate expression is preferably selected for each examination method, each analysis item, and each specimen.

TABLE 1

| | | |
|---|---|---|
| Logistic curve | $E(t) = \dfrac{E_{range}}{1 + \left(\dfrac{t}{a}\right)^k} + E_b$ | (4) |
| Gompertz curve | $E(t) = E_{range} \times \exp\left(-\exp\left(-\left(\dfrac{t-a}{k}\right)\right)\right) + E_b$ | (5) |
| Hill | $E(t) = E_{range} \times t^{\frac{t^k}{b^k + t^k}} + E_b$ | (6) |
| Chapman | $E(t) = E_{range} \times (1 - \exp(-kt))^b + E_b$ | (7) |

REFERENCE SIGNS LIST

100 automatic analyzing apparatus
101 sample probe
102 sample disk
103 sample vessel
104 reaction vessel
105 sample syringe pump
106 reagent probe
107 reagent disc
108 reagent vessel
109 reagent heater
110 reagent syringe pump
111 reaction vessel storage
112 vessel carrier
113 detection unit
114 reaction vessel setting unit
115 light source
116 detection unit (optical sensor)
117 waste box
118 operation computer
119 hard disk
120 controller computer
121 A/D converter
122 interface
123 printer

The invention claimed is:
1. An automatic analyzing apparatus comprising:
a detection unit configured to measure a coagulation index that indicates an amount of coagulated blood in a blood sample in which a reagent has been dispensed;
a first curve fitting function configured to calculate, at a predetermined time interval, a parameter for an approximate curve of a coagulation curve by curve fitting, based on the measured coagulation index;
an early reaction checking function configured to determine whether there is an early coagulation index change, based on the parameter for the approximate curve calculated at the predetermined time interval by the first curve fitting function, the early coagulation index change indicating a region in which the coagulation index increases immediately after the reagent is dispensed in the sample; and a clotting time calculation function configured to calculate a clotting time, based on whether there is the early coagulation index change.

2. The automatic analyzing apparatus according to claim 1, further comprising:

a plateau phase deciding function configured to determine whether a first coagulation reaction has been completed when it is determined that there is the early coagulation index change;

a second curve fitting function configured to calculate a parameter for an approximate curve of the coagulation curve at a predetermined time interval by curve fitting when it is determined that the first coagulation reaction has been completed, based on the detected coagulation index that is not subjected to the curve fitting by the first curve fitting function; and a parameter convergence checking function configured to determine whether the parameter of the approximate curve has converged to a constant value, the parameter being calculated at the predetermined time interval, wherein the clotting time calculation function calculates the clotting time when it is determined that there is the early coagulation index change and when the parameter for the approximate curve converges to a constant value, the parameter being calculated at the predetermined time interval by the second curve fitting function, based on an approximate function representing the approximate curve determined by the parameter calculated by the second curve fitting function.

3. The automatic analyzing apparatus according to claim 2, further comprising:

a lag time deciding function configured to determine a beginning point of lag time that indicates a point from which the coagulation reaction begins in the coagulation curve when the parameter for the approximate curve converges to a constant value, the parameter being calculated at the predetermined time interval by the first curve fitting function, based on the converged parameter for the approximate curve; and a third curve fitting function configured to calculate a parameter for an approximate curve of the coagulation curve from the coagulation index by curve fitting between the beginning point of the lag time and a measurement end point indicating a point of measurement completion, wherein the clotting time calculation function calculates the clotting time when it is determined that there is the early coagulation index change and when the parameter for the approximate curve converges to a constant value, the parameter being calculated at the predetermined time interval by the second curve fitting function, based on an approximate function representing the approximate curve determined by the parameter calculated by the second curve fitting function, and the clotting time calculation function calculates the clotting time when it is determined that there is no early coagulation index change and when the parameter for the approximate curve converges to a constant value, the parameter being calculated at the predetermined time interval by the first curve fitting function, based on an approximate function representing the approximate curve determined by the parameter calculated by the third curve fitting function.

4. The automatic analyzing apparatus according to claim 1, further comprising:

a parameter convergence checking function configured to determine whether the parameter of the approximate curve has converged to a constant value, the parameter being calculated at the predetermined time interval;

a lag time deciding function configured to determine a beginning point of lag time that indicates a point from which the coagulation reaction begins in the coagulation curve when the parameter of the approximate curve converges to a constant value, the parameter being calculated at the predetermined time interval by the first curve fitting function, based on the converged parameter of the approximate curve; and a third curve fitting function configured to calculate a parameter for an approximate curve of the coagulation curve from the coagulation index by curve fitting between the beginning point of the lag time and a measurement end point indicating a point of measurement completion, wherein the clotting time calculation function calculates the clotting time when it is determined that there is no early coagulation index change and when the parameter for the approximate curve converges to a constant value, the parameter being calculated at the predetermined time interval by the first curve fitting function, based on an approximate function representing the approximate curve determined by the parameter calculated by the third curve fitting function.

5. The automatic analyzing apparatus according to claim 1, wherein an approximate function representing the approximate curve satisfies the following expression:

[Expression 1]

$$E(t) = \frac{E_{range}}{\left\{1 + \exp\left(\frac{t-a}{k}\right)\right\}^b} + E_b$$

where a parameter $E_{range}$ represents a difference between a maximal value $E_p$ and a minimal value $E_b$ of scattered light intensity $E(t)$, a parameter a represents time t at an inflection point of the approximate curve, a parameter k represents a gradient of a curve in a region interposed between a baseline region and a plateau region in the approximate curve, and a parameter b represents a parameter for correction, wherein the early reaction checking function determines that there is the early coagulation index change when neither of the parameters $E_{range}$ and k of the approximate curve is zero, the parameters $E_{range}$ and k being calculated at the predetermined time interval by the first curve fitting function.

6. An analyzing method comprising:

a detection process of measuring a coagulation index that indicates an amount of coagulated blood in a blood sample in which a reagent has been dispensed;

a first curve fitting process of calculating, at a predetermined time interval, a parameter for an approximate curve of a coagulation curve by curve fitting, based on the measured coagulation index;

an early reaction checking process of determining whether there is an early coagulation index change, the early coagulation index change indicating a region in which the coagulation index increases immediately after the reagent is dispensed in the sample, based on the parameter for the approximate curve calculated at the predetermined time interval by the first curve fitting process; and a clotting time calculation process of calculating a clotting time, based on whether there is the early coagulation index change.

* * * * *

UNITED STATES PATENT AND TRADEMARK OFFICE
CERTIFICATE OF CORRECTION

Page 1 of 1

PATENT NO. : 9,581,609 B2
APPLICATION NO. : 14/777550
DATED : February 28, 2017
INVENTOR(S) : Chie Yabutani, Akihisa Makino and Sakuichiro Adachi It is certified that error appears in the above-identified patent and that said Letters Patent is hereby corrected as shown below:

On the Title Page

Please add the following:
(30)     Foreign Application Priority Data
April 2, 2013    (JP).............................2013-077183

Signed and Sealed this
Twenty-fourth Day of October, 2017

Joseph Matal
*Performing the Functions and Duties of the
Under Secretary of Commerce for Intellectual Property and
Director of the United States Patent and Trademark Office*